United States Patent [19]

Tomcufcik

[11] 3,941,825

[45] Mar. 2, 1976

[54] SUBSTITUTED AMINOBENZYLIDENEAMINO GUANIDINE COMPOUNDS

[75] Inventor: Andrew Stephen Tomcufcik, Old Tappan, N.J.

[73] Assignee: American Cyanamid Company, Stamford, Conn.

[22] Filed: Nov. 7, 1974

[21] Appl. No.: 521,716

Related U.S. Application Data

[60] Division of Ser. No. 383,419, July 27, 1973, Pat. No. 3,901,944, which is a continuation-in-part of Ser. No. 251,096, May 8, 1972, abandoned, which is a continuation-in-part of Ser. No. 94,591, Dec. 2, 1970, Pat. No. 3,769,432, which is a continuation-in-part of Ser. No. 833,167, June 13, 1969, abandoned, which is a continuation-in-part of Ser. No. 741,247, July 1, 1968, abandoned.

[52] U.S. Cl. ........... 260/465 E; 260/457; 260/564 F
[51] Int. Cl.$^2$........................................ C07C 133/12
[58] Field of Search............. 260/564 F, 457, 465 E

[56] References Cited

UNITED STATES PATENTS

| | | | |
|---|---|---|---|
| 3,130,232 | 4/1964 | Paquette...................... | 260/564 F |
| 3,456,059 | 7/1969 | Wick et al...................... | 260/564 F |
| 3,795,692 | 3/1974 | Kulsa et al...................... | 260/564 F |

OTHER PUBLICATIONS

Chemical Abstracts, Vol. 51, Col. 14, 559(f).

*Primary Examiner*—Gerald A. Schwartz
*Attorney, Agent, or Firm*—Denis A. Polyn

[57] ABSTRACT

The preparation of 1-amino-3-(4- and 3,4-substituted benzylideneamino)guanidine and the acid addition salts thereof, and their use as intermediates in the preparation of 1,3-bis(4- and 3,4-substituted benzylideneamino)guanidines and their acid addition salts.

The final compounds prepared from the present intermediates have antiprotozoal activity particularly against coccidiosis and malaria.

6 Claims, No Drawings

SUBSTITUTED AMINOBENZYLIDENEAMINO GUANIDINE COMPOUNDS

This application is a division of my application Ser. No. 383,419, filed July 27, 1973, now U.S. Pat. No. 3,901,944 which is a continuation-in-part of my application Ser. No. 251,096, filed May 8, 1972, now abandoned, which is a continuation-in-part of my application Ser. No. 94,591, filed Dec. 2, 1970, now U.S. Pat. No. 3,769,432, which is a continuation-in-part of application Ser. No. 833,167, filed June 13, 1969, now abandoned, which is a continuation-in-part of application Ser. No. 741,247, filed July 1, 1968, now abandoned.

PRIOR APPLICATIONS

In my original application, Ser. No. 741,247, compounds which are substituted guanidines of the following structure are claimed:

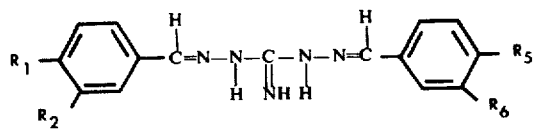

wherein $R_1$ and $R_5$ are halogen, trifluoromethyl or cyano, $R_2$ and $R_6$ are hydrogen or halogen, and the pharmacologically acceptable acid salts thereof.

Subsequently, a continuation-in-part application Ser. No. 833,167 was filed June 13, 1969 in which compounds which are substituted guanidines of the following structure are claimed:

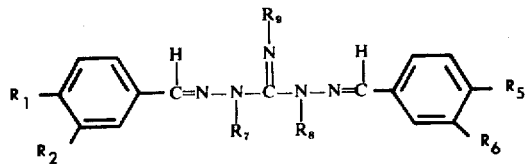

wherein $R_1$ and $R_5$ are halogen, trifluoromethyl or cyano, $R_2$ and $R_6$ are hydrogen or halogen, $R_7$ and $R_8$ are hydrogen or lower alkyl ($C_1$-$C_4$) and $R_9$ is hydrogen or lower alkanoyl ($C_1$-$C_4$) and the pharamacologically acceptable acid salts thereof.

Subsequently, a continuation-in-part application Ser. No. 94,591 was filed in which compounds which are substituted guanidines of the following structure are claimed:

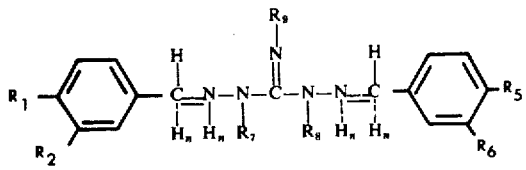

wherein $R_1$ and $R_5$ are selected from the group consisting of halogen, trifluoromethyl, trifluoromethoxy, and cyano; $R_2$ and $R_6$ are selected from the group consisting of hydrogen and halogen; $R_7$ and $R_8$ are selected from the group consisting of hydrogen and lower alkyl, and $R_9$ is selected from the group consisting of hydrogen and lower alkanoyl, $=\!\!=$ is a single or double bond, $n$ is an integer selected from 0 and 1 with the proviso that when $=\!\!=$ is a double bond then $n$ is 0 and when $=\!\!=$ is a single bond, then $n$ is 1, and the pharamacologically acceptable acid salts thereof.

Upon requirement for restriction in Ser. No. 94,591 an application Ser. No. 251,096 was filed and was directed to compounds of the following structure:

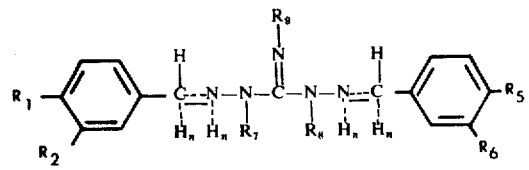

wherein $R_1$ and $R_5$ are selected from the group consisting of halogen, trifluoromethyl, trifluoromethoxy, and cyano; $R_2$ and $R_6$ are selected from the group consisting of hydrogen and halogen; $R_7$ and $R_8$ are selected from the group consisting of hydrogen and lower alkyl; and $R_9$ is selected from the group consisting of hydrogen and lower alkanoyl, $=\!\!=$ is a single or double bond, $n$ is an integer selected from 0 and 1 with the proviso that when $=\!\!=$ is a double bond then $n$ is 0 and when $=\!\!=$ is a single bond, then $n$ is 1, and the pharmacologically acceptable acid salts thereof.

The acid salts can be, for example, nitrate, hydrochloride, hydrobromide, methosulfate, and the like.

The term loweralkyl is intended to include those having 1 to 4 carbon atoms and the term lower alkanoyl, those having 1 to 4 carbons in addition to the carbonyl group. The term halogen includes chlorine, bromine, fluorine, and iodine.

The compounds of this invention are, in general, crystalline solids, ranging in color from white to pale yellow, slightly soluble in water and lower alcohols and insoluble in benzene, toluene and chloroform.

DESCRIPTION OF THE INVENTION

The present invention is directed to intermediates useful in the preparation of the above described compounds. These intermediates can be illustrated by the following formula:

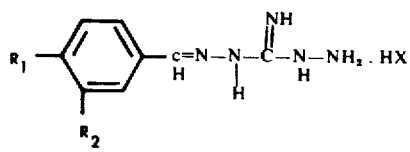

wherein $R_1$ is selected from the group consisting of halogen, trifluoromethyl, trifluoromethoxy and cyano, $R_2$ is hydrogen or chlorine and HX is an acid addition salt.

Certain of the above active novel compounds can be prepared by reacting a compound of the formula:

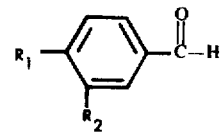

wherein $R_1$ and $R_2$ are as hereinabove described, dissolved in an organic solvent, with an alcoholic or aqueous alcoholic solution of from a molar equivalent to a 100% excess of a compound of the formula:

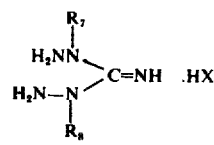

wherein $R_7$ is as hereinabove described and X is the anion of a pharmacologically acceptable acid. The mixture is heated to from 50°C. to the boiling point of the solvent and held there for from 1 to 10 minutes and then cooled to room temperature. The precipitated product is collected, washed with ethanol and/or ether and dried.

Other methods of preparing the instant compounds are illustrated by the equations which follow:

A.

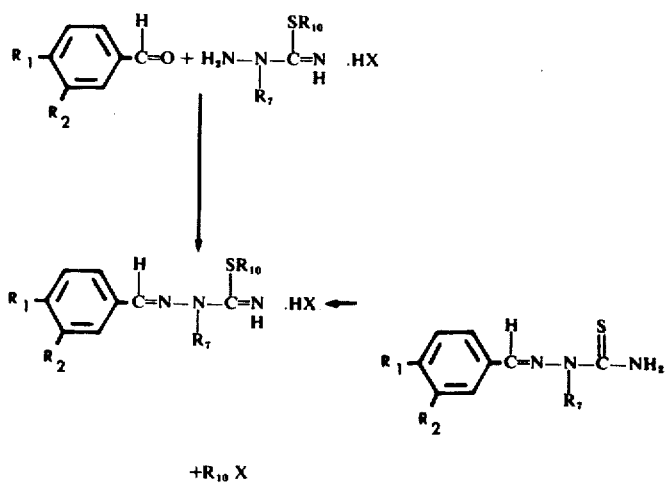

B.

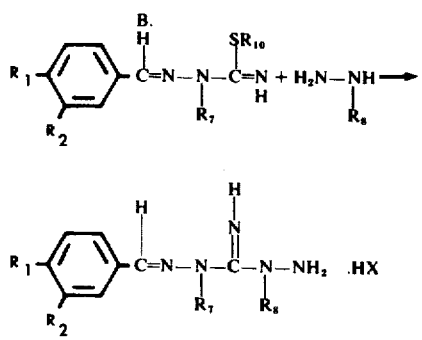

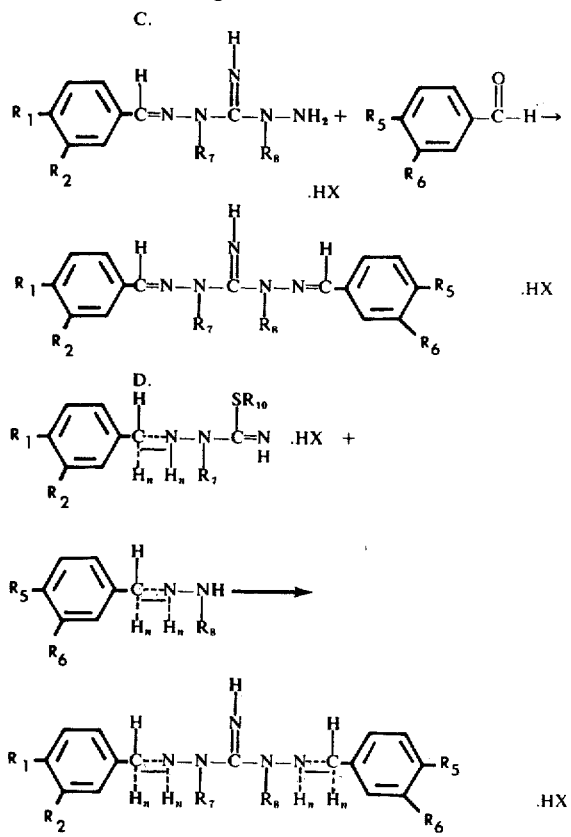

wherein $R_1$, $R_2$, $R_5$, $R_6$, $R_7$, $R_8$, $=$, n and X are as hereinabove described and $R_{10}$ is lower alkyl.

Some of the instant compounds herein described, wherein $R_1$ and $R_5$ are the same, $R_2$ and $R_6$ are the same, $R_7$ and $R_8$ are the same, and $R_9$ is hydrogen, are prepared by the equation illustrated as follows:

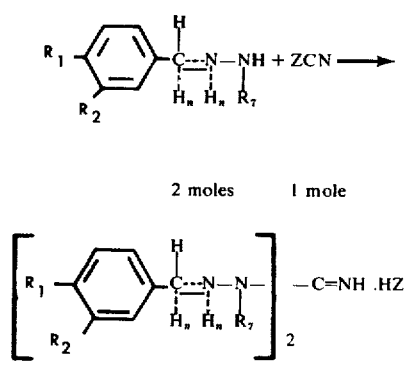

where $R_1$, $R_2$, $R_7$, $=$ and n are as hereinabove described and Z is chlorine or bromine.

Compounds in which $R_9$ is loweralkanoyl are prepared by reaction of the compounds in which $R_9$ is H with the appropriate organic acid anhydride.

E. The following process is directed to a lithium aluminum hydride reduction of the bis(benzylideneamino) guanidine to yield the dihydro derivative of the parent. The process is generally carried out in anhydrous ether under an inert atmosphere, such as a blanket of nitrogen. The reaction is illustrated below.

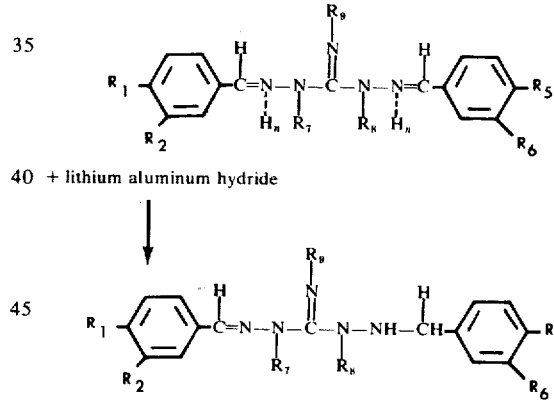

wherein $R_2$, $R_6$, $R_7$, $R_8$ and $R_9$ are as heretofore described and $R_1$ and $R_5$ are halogen, trifluoromethyl or trifluoromethoxy.

Among the novel compounds within the scope of the present invention are the following: 1,3-bis(4-chlorobenzylideneamino)guanidine nitrate, 1,3-bis(4-chlorobenzylideneamino)guanidine hydrochloride, 1,3-bis(4-chlorobenzylideneamino)guanidine methosulfate, 1,3-bis(4-bromobenzylideneamino)guanidine nitrate, 1,3-bis(4-bromobenzylideneamino)guanidine hydrochloride, 1,3-bis(3,4-dichlorobenzylideneamino)guanidine nitrate, 1,3-bis(3,4-dichlorbenzylideneamino)guanidine hydrochloride, 1,3-bis(4-cyanobenzylideneamino)guanidine nitrate, 1,3-bis(4-cyanobenzylideneamino)guanidine hydrochloride, 1-(4-bromobenzylideneamino)-3-(4-cyanobenzylideneamino) guanidine hydrobromide, 1-(4-bromobenzylideneamino)-3-(4-chlorobenzylideneamino)guanidine hydrochloride, 1-(4- chlorobenzylideneamino)-3-[4-(triflouromethyl)benzylideneamino]guanidine hydrochloride, 1,3-bis(4-chlorobenzylideneamino)-1,3-dimethylguanidine, 1,3-bis(4-chlorobenzylideneamino)-1,3-dibutylguanidine hydrobromide, 1,3-bis(4-chlorobenzylideneamino)-2-acetylguanidine, and 1,3-bis(4-chlorobenzylidene)-1-methylguanidine hydrobromide.

The active components and novel compounds of the present invention are highly active antiprotozoal agents in warmblooded animals. For example, these compounds have anticoccidial activity against *Eimeria tenella* as shown by the following test: The animals were Peterson Cross Cockerels, 7 days old and of approximately equal size and weight. These cockerels were divided into groups and the groups were placed in separate cages with wire floors. Medicated and control diets were then presented to the groups of birds 2 days before inoculation while they were still in uncontaminated quarters. During the entire period of the tests, the birds ate and drank ad libitum. Control groups were maintained on a standard unmedicated commercial type chicken diet. Test groups were maintained on the same standard diet in which a measured concentration of test compound had been incorporated homogeneously. The cockerels were inoculated once orally with sporulated oocysts of *Eimeria tenella*. The number of oocysts inoculated directly into the crops of all cockerels in the tests was sufficient to produce high mortality in the untreated controls. The quantity necessary to produce high mortality was determined prior to the times of inoculation by giving graded quantities of oocysts to comparable birds. Seven days following inoculation the tests were terminated and the mortality rate was recorded for each group. The results of these tests appear in Table I and show conclusively that these compounds are highly effective as anticoccidial agents. The tests represent very severe laboratory challenges, and lower concentrations than those shown would be effective under practical field conditions.

TABLE I

| Compound | Salt | Parts Per Million in Diet | Number of Birds Treated | % Survival |
| --- | --- | --- | --- | --- |
| 1,3-Bis(4-chlorobenzylideneamino)guanidine | Nitrate | 0 | 100 | 32 |
|  |  | 18 | 70 | 77 |
|  |  | 36 | 70 | 96 |
|  |  | 54 | 30 | 100 |
| 1,3-Bis(4-chlorobenzylideneamino)guanidine | Methosulfate | 0 | 40 | 28 |
|  |  | 20 | 39 | 59 |
|  |  | 40 | 40 | 90 |
|  |  | 60 | 40 | 98 |
| 1,3-Bis(4-chlorobenzylideneamino)guanidine | Hydrochloride | 0 | 20 | 20 |
|  |  | 8.5 | 20 | 45 |
|  |  | 17 | 20 | 75 |
|  |  | 33 | 20 | 100 |
| 1,3-Bis(4-bromobenzylideneamino)guanidine | Nitrate | 0 | 20 | 45 |
|  |  | 17 | 20 | 80 |
|  |  | 35 | 20 | 95 |
| 1,3-Bis(3,4-dichlorobenzylideneamino)guanidine | Nitrate | 0 | 20 | 30 |
|  |  | 60 | 10 | 100 |
| 1,3-Bis(4-cyanobenzylideneamino)guanidine | Nitrate | 0 | 20 | 20 |
|  |  | 30 | 10 | 80 |
|  |  | 60 | 10 | 100 |
| 1,3-Bis(4-iodobenzylideneamino)guanidine | HCl | 0 | 20 | 0 |
|  |  | 30 | 20 | 55 |
| 1,3-Bis(4-fluorobenzylideneamino)guanidine | Nitrate | 0 | 20 | 45 |
|  |  | 93 | 5 | 80 |
| 1,3-Bis(4-trifluoromethylbenzylideneamino)guanidine | Hydrochloride | 0 | 20 | 70 |
|  |  | 120 | 10 | 100 |
| 1,3-Bis(4-chlorobenzylideneamino)-1,3-dimethylguanidine | Hydrobromide | 0 | 40 | 45 |
|  |  | 30 | 10 | 100 |
|  |  | 120 | 5 | 100 |
| 2-Acetyl-1,3-bis(4-chlorobenzylideneamino)guanidine | — | 0 | 60 | 47 |
|  |  | 5 | 20 | 67 |
|  |  | 10 | 20 | 95 |
|  |  | 30 | 5 | 100 |
| 1-(4-chlorobenzylamino)-3-(4-chlorobenzylideneamino)guanidine | — | 15 | 10 | 90 |
|  |  | 30 | 10 | 100 |
| 1,3-bis(4-trifluoromethoxybenzylideneamino)guanidine | Hydrochloride | 0 | 20 | 55 |
|  |  | 5 | 10 | 80 |

TABLE I-continued

| Compound | Salt | Parts Per Million in Diet | Number of Birds Treated | % Survival |
|---|---|---|---|---|
| | | 10 | 10 | 100 |
| 1,3-bis(4-chloro-benzylamino)guanidine | Hydrochloride | 0 | 20 | 60 |
| | | 10 | 10 | 90 |
| | | 15 | 10 | 90 |
| | | 20 | 10 | 100 |

The compounds of the present invention have high activity against other coccidial species in chickens. Thus, 1,3-bis(4-chlorobenzylideneamino)guanidine completely protected treated chickens from mortality due to *Eimeria necatrix*, and from poor weight gains due to *E. acervulina*, *E. brunetti*, *E. maxima* or *E. mivati*. Methods used were essentially identical with those previously cited with appropriate modifications. Weight gains were determined 7 days after single experimental inoculations with the designated species of coccidia. The results are summarized in Table II.

TABLE II

Anticoccidial Activity of 1,3-Bis(4-chlorobenzylideneamino)guanidine

| Eimeria Spp. | Ppm in Diet | No. Birds | % Survival | % control Weight gain | Salt |
|---|---|---|---|---|---|
| necatrix | 0 | 19 | 21 | 31 | methosulfate |
| | 15 | 20 | 100 | 80 | |
| | 30 | 20 | 100 | 103 | |
| acervulina | 0 | 20 | 100 | 57 | nitrate |
| | 45 | 20 | 100 | 99 | |
| brunetti | 0 | 20 | 100 | 76 | hydrochloride |
| | 15 | 20 | 100 | 100 | |
| | 30 | 20 | 100 | 95 | |
| maxima | 0 | 20 | 100 | 58 | hydrochloride |
| | 15 | 20 | 100 | 101 | |
| | 30 | 20 | 100 | 95 | |
| | 45 | 20 | 100 | 100 | |
| mivati | 0 | 20 | 95 | 52 | hydrochloride |
| | 15 | 20 | 100 | 86 | |
| | 30 | 20 | 100 | 91 | |
| | 45 | 20 | 100 | 100 | |

In the Lieber et al. reference J. Org. Chem. Vol. 17, pages 518–522 (1952) there are described compounds in Table I which may be considered position isomers or homologues or analogs of the present compounds. However, these compounds have been found inactive (with one exception) as anti-coccidial agents. Numbering the compounds of Table I in the Lieber et al. reference from 1 to 17 the results of the testing for anti-coccidial activity is as follows:

TABLE III

| Prior art Compounds (Derivatives of 1,3-diaminoguanidine) | | Dosage (parts) per million | Activity |
|---|---|---|---|
| 4) o-chlorobenzaldehyde | | 120 | inactive |
| 5) o-chlorobenzaldehyde | | 120 | inactive |
| 6) p-hydroxybenzaldehyde | | 125 | inactive |
| 7) m-nitrobenzaldehyde | | 120 | inactive |
| 8) m-nitrobenzaldehyde | | 120 | inactive |
| 9) piperonal | | 125 | inactive |
| 11) salicylaldehyde | | 125 | inactive |
| 12) salicylaldehyde | | 200 | inactive |
| 14) acetophenone | | 250 | inactive |
| 17) p-bromoacetophenone | | 120 | active |
| 17) p-bromoacetophenone | | 60 | inactive |

Compounds of Present Invention (Derivatives of 1,3-

TABLE III-continued

| Prior art Compounds (Derivatives of 1,3-diaminoguanidine) | | Dosage (parts) per million | Activity |
|---|---|---|---|
| Diaminoguanidine) | | | |
| p-chlorobenzaldehyde | (nitrate) | 18 | active |
| p-chlorobenzaldehyde | (methosulfate) | 20 | active |
| p-chlorobenzaldehyde | (hydrochloride) | 8.5 | active |
| p-bromobenzaldehyde | (nitrate) | 17 | active |
| p-iodobenzaldehyde | (hydrochloride) | 30 | active |

The compounds of the present invention most closely related to the prior art are active at relatively low dosages whereas the only prior art compound of the reference (compound 17) was active only at 120 p.p.m.

It is anticipated that the compounds of this invention will prove widely useful in a variety of vehicles, modes or means of administration or dispersal for the purpose of minimizing, preventing, controlling, treating, ameliorating or curing protozoal infections with sensitive organisms. One of these infections is coccidiosis which is a protozoal parasitic disease widespread in animals, causing a greater economic loss among domestic and game animals in temperate climates than any other protozoan disease. Coccidiosis is the most important animal parasitic disease of chickens, the causative agents being protozoa of the genus Eimeria, and is also important in other domestic animals such as turkeys, sheep, cattle and pigs.

The present compositions and novel compounds are active in warn-blooded animals as anti-malarial agents. When tested in mice in the range of from 150 mg./kg.

to 300 mg./kg. they show an activity comparable to quinine.

Although administration of the compounds for coccidiosis will generally be most practical in or with the feed, or in the drinking water, the compounds may also be administered to individual hosts in the form of tablets, drenches, capsules or the like, or by injection. These latter methods of administration are, of course, less practical for treatment of large groups of animals than they are for treating limited numbers of animals, but they are quite practical for use on a small scale or on an individual basis.

With the compounds of the instant invention, medicated feeds are usually prepared by thoroughly admixing about 0.0005 to 0.05% by weight and preferably about 0.0015 to 0.025% by weight of active compound with a nutritionally balanced animal feed, as for example, the chick feed described in the examples hereinafter.

Where it is desirable to prepare a concentrate or premix for ultimate dilution in feed to the above levels, generally about 1 to 25% and preferably about 3 to 10% by weight of medicament is blended with an edible organic or inorganic carrier, e.g., corn meal or corn soybean meal, or alfalfa, or mineral salts containing a small amount of an edible dusting oil such as, for example, corn oil, or soybean oil. The thus prepared premix may then be added to the complete animal poultry feed prior to administration.

DETAILED DESCRIPTION

The following examples describe in detail the preparation of representative compounds of the present invention. In these examples the starting materials, 4-chlorobenzaldehyde, 4-bromobenzaldehyde, 3,4-dichlorobenzaldehyde, and 4-cyanobenzaldehyde are each widely used chemical reagents available from commercial sources. The compound 1,3-diaminoguanidine nitrate, or methosulfate may be prepared as described by Keim, Henry and Smith, Journal of the American Chemical Society, 72, 4944–4964 (1950). The preparation of the compound 1,3-diaminoguanidine hydrochloride is shown in Phillips and Williams, ibid, 50, 2465 (1928). The synthesis of 1,3-diamino-1-methylguanidine hydrobromide is shown by Kroeger, et al., Ann. 664 156 (1963). The preparation of 1,3-diamino-1,3-dimethylguanidine hydrobromide is described by McBride, et al., J. Org. Chem. 22 152 (1957).

EXAMPLE 1

Preparation of
1,3-Bis(4-chlorobenzylideneamino)guanidine nitrate, hydrochloride and methosulfate A boiling solution of 14.1 grams of 4-chlorobenzaldehyde (slight excess) in 250 milliliters of ethanol is stirred vigorously as a solution of 6.1 grams of 1,3-diaminoguanidine nitrate and 0.5 milliliters of concentrated nitric acid in 50 milliliters of water is added in one portion. The reaction mixture is stirred as the temperature recedes to room temperature. The reaction mixture is then allowed to stand for several hours. The precipitate which forms is collected, washed with hot ethenol, air-dried and finally dried at 60°C. under reduced pressure. The yield is 14.0 grams of product and the melting point is 198°C. with decomposition.

The hydrochloride or methosulfate salt may be prepared by this same procedure, substituting equivalent amounts of the appropriate guanidine salt and employing 0.5 milliliters of the appropriate acid. The hydrochloride salt melts at 289°–290°C. with decomposition. The methosulfate salt melts at 217°–224°C. with decomposition.

EXAMPLE 2

Preparation of
1,3-Bis(4-chlorobenzylideneamino)guanidine

The free base of the title compound is prepared by suspending 8 g. of the nitrate salt (Example 1) in 200 ml. of anhydrous ethanol, adding 2.5 ml. of 10N sodium hydroxide solution, stirring and heating until the reaction mixture becomes homogeneous, and finally cooling the solution and filtering the resultant solid. The melting point of the free base is 187°–188°C.

EXAMPLE 3

Preparation of
1,3-Bis(4-bromobenzylideneamino)guanidine Nitrate

A boiling solution of 20.0 grams of 4-bromobenzaldehyde in 250 milliliters of ethanol is stirred vigorously as a solution of 6.1 grams of 1,2-diaminoguanidine nitrate and 0.5 milliliters of concentrated nitric acid in 50 milliliters of water is added in one portion. The reaction mixture is stirred as the temperature recedes to room temperature. The reaction mixture is allowed to stand for several hours. The precipitate which forms is collected, washed with hot ethanol, air dried and finally dried at 60°C. under reduced pressure. The yield is 16.5 grams of product and the melting point is 178°–180°C. with decomposition.

EXAMPLE 4

Preparation of
1,3-Bis(3,4-dichlorobenzylideneamino)guanidine Nitrate

A boiling solution of 17.6 grams of 3,4-dichlorobenzaldehyde in 250 milliliters of ethanol is stirred vigorously as a solution of 6.1 grams of 1,3-diaminoguanidine nitrate and 0.5 milliliters of concentrated nitric acid in 50 milliliters of water is added in one portion. The reaction mixture is stirred as the temperature recedes to room temperature. The reaction mixture is then allowed to stand for several hours. The precipitate which forms is collected, washed with hot ethanol, air dried and finally dried at 60°C. under reduced pressure. The yield is 17.5 grams of product and the melting point is 195°–196°C. with decomposition.

EXAMPLE 5

Preparation of
1,3-Bis(4-cyanobenzylideneamino)guanidine Nitrate

A boiling solution of 13.1 grams of 4-cyanobenzaldehyde in 250 milliliters of ethanol is stirred vigorously as a solution of 6.1 grams of 1,3-diaminoguanidine nitrate and 0.5 milliliters of concentrated nitric acid in 50 milliliters of water is added in one portion. The reaction mixture is stirred as the temperature recedes to room temperature. The reaction mixture is then allowed to stand for several hours. The precipitate which forms is collected, washed with hot ethanol, air dried and finally dried at 60°C. under reduced pressure. The yield is 15.1 grams of product and the melting point is 205°–210°C. with decomposition.

EXAMPLE 6

Preparation of 1,3-Bis(4-iodobenzylideneamino)guanidine Hydrochloride

Following the procedure of Example 1 and substituting 4-iodobenzaldehyde for 4-chlorobenzaldehyde and 1,2-diaminoguanidine hydrochloride for 1,3-diaminoguanidine nitrate the product of the example is obtained. The hydrochloride has a melting point of 288°–291°C., dec.

EXAMPLE 7

Preparation of 1,3-Bis(4-fluorobenzylideneamino)guanidine Nitrate

Using the procedure of Example 1 and substituting 4-fluorobenzaldehyde for 4-chlorobenzaldehyde the product of the example is obtained. The nitrate has a melting point of 169°–170°C., dec.

EXAMPLE 8

Preparation of Methyl thiocarbazimidate hydrochloride

Excess methyl chloride is collected in a dry iceacetone-cooled trap and added to a tared pressure vessel containing 91.1 g. of powdered thiosemicarbazide in 600 ml. of anhydrous ethanol. Weighing the vessel plus contents shows that 53 g. of methyl chloride has been added. The reaction mixture is magnetically stirred while heating in an oil bath temperature of 77° to 110°C. for 48 minutes. After 33 minutes, the reaction has become homogeneous. It is cooled in ice and the resultant rose-white solid filtered and dried in a vacuum oven. The yield of the title compound is 121 g. melting point 154°–155°C.

Substitution of dimethyl sulfate, ethyl iodide or propyl bromide for methyl chloride and allowing the reactions to proceed in refluxing anhydrous ethanol instead of under pressure, results in the preparation of methyl thiocarbazimidate methosulfate, ethyl thiocarbazimidate hydroiodide, and propyl thiocarbazimidate hydrobromide, respectively.

EXAMPLE 9

Preparation of Methyl 3-(4-chlorobenzylidene)thiocarbazimidate hydrochloride A solution of 3.8 g. of 4-chlorobenzaldehyde in 10 ml. of warm absolute ethanol is added all at once to a stirred solution of 5 g. of methyl thiocarbazimidate hydrochloride in 100 ml. of warm absolute alcohol. The reaction mixture is stirred at room temperature for about 15 minutes and cooled in ice. The white solid product is filtered off and air dried; melting point 212°–214°C.

The following are prepared in like manner: methyl 3-(4-bromobenzylidene)thiocarbazimidate methosulfate from 4-chlorobenzaldehyde and methyl thiocarbazimidate methosulfate, ethyl 3-(4-cyanobenzylidine)thiocarbazimidate hydroiodide from 4-cyanobenzaldehyde and ethyl thiocarbazimidate hydroiodide, and propyl 3-(3,4-dichlorobenzylidene)thiocarbazimidate hydrobromide from 3,4-dichlorobenzaldehyde and propyl thiocarbazimidate hydrobromide.

EXAMPLE 10

Preparation of Methyl 3-(4-chlorobenzylidene)thiocarbazimidate hydrochloride A 10% molar excess of methyl chloride is added to 2.14 g. of 4-chlorobenzaldehyde thiosemicarbazone and 25 ml. of a anhydrous ethanol in a pressure vessel. The reaction mixture is magnetically stirred and heated in an oil bath for 1½ hour. The crystalline title compound separates on cooling and is filtered off and air dried.

EXAMPLE 11

Preparation of 1,3-Bis(4-chlorobenzylideneamino)guanidine hydrochloride

A solution of 101 g. of 4-chlorobenzaldehyde in 40 ml. of warm 95% ethanol is added portionwise to a stirred solution of diaminoguanidine hydrochloride in 450 ml. of 90% ethanol at 70°C. Addition of the first portion causes rapid boiling and the reaction mixture is cooled to a little above room temperature before the remainder of the 4-chlorobenzaldehyde solution is added. Stirring is continued for 15 minutes and the reaction mixture is cooled in ice, filtered, and air dried. The yield is 122 g. of solid, melting point 295°C. with decomposition.

The same product is obtained when 1-amino-3-(4-chlorobenzylideneamino)guanidine hydrochloride (Example 13) is allowed to react under similar conditions as above with an equimolar amount of 4-chlorobenzaldehyde.

The same product is also obtained from the reaction of methyl 3-(4-chlorobenzylidene)thiocarbazimidate (Example 10) with the hydrazone of 4-chlorobenzaldehyde in refluxing 95% ethanol. The hydrazone of 4-chlorobenzaldehyde is prepared according to the procedure for the synthesis of hydrazones of aromatic aldehydes and ketones outlined in G. Newkome and D. Fishel, J. Org. Chem., 31 677 (1966).

EXAMPLE 12

Preparation of 1-Amino-3-(4-chlorobenzylideneamino)guanidine Hydrochloride

To a solution of 2.6 g. of methyl 3-(4-chlorobenzylidene)thiocarbazimidate in 10 ml. of boiling absolute ethanol is added 0.6 g. of hydrazine hydrate. The reaction mixture is cooled in ice and the solid 1-amino-3-(4-chlorobenzylideneamino)guanidine removed by filtration. Treatment with ethanolic hydrogen chloride gives the subject compound, melting at 243°–244°C.

Similarly, the reaction of methyl 3-(4-bromobenzylidene)thiocarbazimidate methosulfate, ethyl 3-(4-cyanobenzylidene)thiocarbazimidate hydroiodide, and propyl 3-(3,4-dichlorobenzylidene)thiocarbazimidate hydrobromide with hydrazine yield, respectively, 1-amino-3-(4-bromobenzylideneamino)guanidine methosulfate, 1-amino-3-(4-cyanobenzylideneamino)guanidine hydroiodide, and 1-amino-3-(3,4-dichlorobenzylideneamino)guanidine hydrobromide.

The preparation of the subject compound may also be accomplished as follows: 25 g. of 1,3-diaminoguanidine hydrochloride is dissolved in 1800 ml. of boiling ethanol. To this boiling solution, 28 g. of 4-chlorobenzaldehyde in 300 ml. of ethanol is added over a period of 8 hours. The reaction mixture is then cooled at 0°C. overnight, clarified, and the filtrate concentrated to 500 ml. volume and cooled at 0°C. 29 g. of precipitate is obtained. This is slurried in 300 ml. of water, the pH adjusted to 8–8.5 with sodium hydroxide solution, the slurry heated to boiling and filtered. Cooling and filtrate gives 18 g. of essentially pure product melting at 243°–244°C., as in the previous preparation.

EXAMPLE 13

Preparation of 1-(4-bromobenbylideneamino)-3-(4-chlorobenzylideneamino)guanidine hydrochloride A solution of 1.85 g. of 4-bromobenzaldehyde in 10 ml. of ethanol is added to a solution of 2.48 g. of 1-amino-3-(4-chlorobenzylideneamino)guanidine hydrochloride in 25 ml. of boiling 95% ethanol. The reaction mixture is cooled and the solid product removed by filtration and air dried. It melts at 286-288°C. with decomposition.

In a similar manner the reaction of 1-amino-3-(4-bromobenzylideneamino)guanidine methosulfate with 4-chlorobenzaldehyde gives the methosulfate salt of the subject compound. The reaction of 1-amino-3-(4-cyanobenzylideneamino)guanidine hydroiodide with 4-chlorobenzaldehyde gives 1-(4-chlorobenzylideneamino)-3-(4-cyanobenzylideneamino)guanidine hydroiodide; the reaction of 1-amino-3-(4-chlorobenzylideneamino)guanidine hydrochloride with 4-cyanobenzaldehyde affords the corresponding hydrochloride salt which melts at 297°–298°C. The reaction of 1-amino-3-(3,4-dichlorobenzylideneamino)guanidine hydrobromide and 4-chlorobenzaldehyde gives 1-94-chlorobenzylideneamino)-3-(3,4-dichlorobenzylidenamino)guanidine hydrobromide; the reaction of 1-amino-3-(4-chlorobenzylideneamino)guanidine hydrochloride with 3,4-dichlorobenzaldehyde gives the corresponding hydrochloride salt which melts at 288°C.

EXAMPLE 14

Preparation of 1-Amino-3-[(4-trifluoromethyl)benzylideneamino]guanidine Hydrochloride An ether solution of 34.8 g. of 4-(trifluoromethyl)benzaldehyde is slowly added to a hot (70°–80°C.) solution of 41.5 g. (50% excess) of 1,3-diaminoguanidine hydrochloride in aqueous ethanol. The slow addition rate permits the ether to boil off, and a slow reaction mixture is maintained. After heating an additional thirty minutes, the mixture is cooled and taken to dryness under vacuum. The solid residue is extracted with water to remove the excess 1,3-diaminoguanidine hydrochloride, and with hot ethanol to remove any 1,3-bis[(4-trifluoromethyl)benzylideneamino]guanidine hydrochloride present. The insoluble residue (14.4 g.) is essentially pure 1-amino-3-[(4-trifluoromethyl)benzylideneamino]guanidine hydrochloride, melting at 247°–249°C. with dec.

EXAMPLE 15

Preparation of 1-(4-Chlorobenzylideneamino)-3-[(4-trifluoromethyl)benzylideneamino]guanidine Hydrochloride A solution of 1.41 g. of 4-chlorobenzaldehyde in 10 ml. of ethanol is added to a solution of 2.82 g. of 1-amino-3-[4-(trifluoromethyl)benzylideneamino]guanidine hydrochloride in 25 ml. of boiling 95% ethanol. Cooling the reaction mixture gives the subject compound as a crystalline solid melting at 263°C. Alternatively, under similar reaction conditions, 1.81 g. of 4-(trifluoromethyl)benzaldehyde, and 2.48 g. of 1-amino-3-(4-chlorobenzylideneamino)guanidine hydrochloride yield the same product.

Replacement of the 4-chlorobenzaldehyde by an equivalent of 4-bromobenzaldehyde gives 1-(4-bromobenzylideneamino)-3-[4-(trifluoromethyl)benzylideneamino]guanidine hydrochloride, melting at 265°–268°C. Similarly, 3,4-dichlorobenzaldehyde yields 1-(3,4-dichlorobenzylideneamino)-3-8 4-(trifluoromethyl)benzylideneamino]guanidine hydrochloride, melting at 265°–268°C., and 4-cyanobenzaldehyde yields 1-(4-cyanobenzylideneamino)-3-[(4-trifluoromethyl)benzylideneamino]guanidine hydrochloride, melting at 269°–271°C. Alternatively, the latter three compounds may also be prepared by the reaction of 4-(trifluoromethyl)benzaldehyde and 1-amino-3-(4-bromobenzylideneamino)guanidine hydrochloride, 1-amino-3-(3,4-dichlorobenzylideneamino)guanidine hydrochloride, and 1-amino-3-(4-cyanobenzylideneamino)guanidine hydrochloride, respectively.

EXAMPLE 16

Preparation of Chick Diet

The following specific feed composition is an example of poultry feed as a carrier for the coccidiostats described hereinbefore.

| | |
|---|---|
| Vitamin-Amino acid | 0.5% |
| Trace Minerals | 0.1% |
| Sodium Chloride | 0.3% |
| Dicalcium Phosphate | 1.2% |
| Ground Limestone | 0.5% |
| Stabilized Fat | 4% |
| Dehydrated Alfalfa, 17% protein | 2% |
| Corn Gluten Meal, 41% protein | 5% |
| Menhaden Fish Meal, 60% protein | 5% |
| Soybean Oil Meal, 44% protein | 30% |
| Ground Yellow Corn, Fine To | 100% |

The vitamin pre-mix in the above feed composition is prepared from the following formulation. The expressions of quantity relate to units per kilogram of the feed composition.

| | |
|---|---|
| Butylated Hydroxy toluene | 125 mg. |
| di-Methionine | 500 mg. |
| Vitamin A | 3300 I.U. |
| Vitamin $D_3$ | 1100 I.C.U. |
| Riboflavin | 4.4 mg. |
| Vitamin E | 2.2 I.U. |
| Niacin | 27.5 mg. |
| Pantothenic Acid | 8.8 mg. |
| Choline Chloride | 500 mg. |
| Folic Acid | 1.43 mg. |
| Menadione Sodium Bisulfate | 1.1 mg. |
| Vitamin $B_{12}$ | 11 mcg. |
| Ground Yellow Corn, Fine To | 5 gm. |

EXAMPLE 17

Preparation of
1,3-Bis(4-trifluoromethylbenzylideneamino)guanidine hydrochloride A solution of 10 g. of 4-trifluoromethylbenzaldehyde in the minimum amount of 95% ethanol is added to a boiling solution of 3.6 g. of diaminoguanidine hydrochloride in 50 ml. of 95% ethanol and a few ml. of water. The solution is stirred and allowed to cool and the solid removed by filtration and washed with 95% ethanol and ether. The yield is 9.6 g. of white solid with a melting point of 272°–273.5°C. with decomposition.

EXAMPLE 18

Preparation of
1,3-Bis(4-chlorobenzylideneamino)-1,3-dimethylguanidine hydrobromide A mixture of 14.1 grams of 4-chlorobenzaldehyde, 4.6 grams of methylhydrazine and 500 ml. of dried benzene is stirred at reflux in a continuous water removal apparatus until no further separation of water is noted. The benzene solution of the resultant methylhydrazone of 4-chlorobenzaldehyde is cooled to room temperature and treated with a solution of 5.3 grams of cyanogen bromide in 100 ml. of benzene. The reaction mixture is stirred at reflux for 4 hours, a white precipitate separating out during this time. The precipitate is filtered from the hot solution, washed and dried. It is recrystallized from ethanol to yield 4.0 grams of the pure compound melting at 223°–225°C. with decomposition.

The same compound is obtained when two molar equivalents of 4-chlorobenzaldehyde and one molar equivalent of 1,3-diamino-1,3-dimethylguanidine hydrobromide are refluxed in ethanol solution in the presence of a little 48% aqueous hydrobromic acid for a few minutes.

EXAMPLE 19

Preparation of
1,3-Bis(4-chlorobenzylideneamino)-1,3-di-n-butylguanidine hydrobromide The preparation of the above compounds is carried out by the procedure of Example 18, an equivalent of n-butylhydrazine replacing the methylhydrazine. The isolated product after recrystallization from ethanol-diethyl ether decomposes about 150°C.

EXAMPLE 20

Preparation of
1,3-Bis(4-Chlorobenzylideneamino)-1-methylguanidine hydrobromide

The preparation of the title compound is carried out essentially by the procedure of Example 1, 7.3 grams of 1,3-diamino-1-methylguanidine hydrobromide replacing the 1,3-diaminoguanidine nitrate and 0.5 ml. of 48% HBr being employed as catalyst. The yield of product is 15.4 grams and the melting point is 276°–278°C.

EXAMPLE 21

Preparation of
2-Acetyl-1,3-bis(4-chlorobenzylideneaminoguanidine

A mixture of 20 g. of 1,3-bis(p-chlorobenzylideneamino)guanidine free base and 9 ml. of acetic anhydride in 300 ml. of anhydrous ether is stirred at reflux for 16 hours, then filtered to give a solid containing starting material and acetylated material. The solid is reacted with an additional 3 ml. of acetic anhydride in 300 ml. of toluene for 1 hour, cooled to room temperature and filtered. The solid (14 g.) is dissolved in 100 ml. of chloroform and treated with 50 ml. of 3 N hydrochloric acid, and the resulting solid is filtered, the crude product is slurried in 100 ml. of boiling chloroform, filtered, and dried to give 7.2 g. of 2-acetyl-1,3-bis(4-chlorobenzylideneamino)guanidine hydrochloride, melting point 193°–194°C.

The hydrochloride salt is partitioned between chloroform and aqueous sodium bicarbonate, and the chloroform layer is dried and evaporated to give 2-acetyl-1,3-bis(4-chlorobenzylideneamino)guanidine, melting point 197°–200°C. (dec.).

The reaction of 1,3-bis(p-chlorobenzylideneamino)-guanidine free base with acetyl chloride in ether gives the same acetyl derivative according to thin layer chromatographic evidence, along with recovered starting material.

When 1,3-bis(p-chlorobenzylideneamino)-1,3-dimethylguanidine free base is submitted to the above reaction conditions with acetic anhydride, there is obtained the corresponding 2-acetyl-1,3-bis(4-chlorobenzylideneamino)-1,3-dimethylguanidine.

Similarly, the reaction of 1,3-bis(4-cyanobenzylideneamino)guanidine and proprionic anhydride in refluxing ether gives 1,3-bis(4-cyanobenzylideneamino)-2-propionyl)guanidine.

EXAMPLE 22

Preparation of
1-(4-Chlorobenzylamino)-3-(4-chlorobenzylideneamino)guanidine

A mixture of 0.95 g. (0.025 mole) of lithium aluminum hydride in 100 ml. of anhydrous ether is stirred under nitrogen as 4.0 g. (0.012 mole) of 1,3-bis(p-chlorobenzylideneamino)guanidine free base is added in portions over a five-minute period. The reaction turns green, and finally brown with gas evolution during the addition. after adding an additional 100 ml. of ether and stirred at room temperature for 3½ hours, the reaction mixture is poured over 500 ml. of ice-water mixture with stirring, calcium carbonate added to facilitate separation of the phases, and the yellow etheral layer separated. The aqueous layer is washed with 50 ml. of ether, and the combined ether layers washed with two 50 ml. portions of water, then cooled to 5° and filtered to give 1.3 g. of yellow 1-(4-chlorobenzylamino)-3-(4-chlorobenzylideneamino)-guanidine, melting point 170°–173°C. Additional material may be obtained from the mother liquors.

The same compound is synthesized by the reaction of equimolar quantities of p-chlorobenzylhydrazine and methyl-3-(4-chlorobenzylidene)thiocarbazimidate hydrochloride (see Example 10) in hot ethanol. It is also prepared by the reaction of equimolar amounts of 1-(p-chlorobenzyl)-S-methylisothiosemicarbazide and hydrazine in warm ethanol, which affords 1-amino-3-(p-chlorobenzylamino)guanidine, followed by treatment of the latter with an equimolar quantity of p-chlorobenzaldehyde in hot isopropanol.

EXAMPLE 23

Preparation of 1,3-bis(4-Chlorobenzylamino)guanidine Hydroiodide

The starting materials for this reaction are literature compounds and are prepared in the following manner. p-Chlorobenzylhydrazine from heating p-chlorobenzyl chloride with excess hydrazine hydrate in i-propanol and distilling: F. E. Anderson et al., J. Med. and Pharm. Chem., 5, 221 (1962). 1-(p-chlorobenzyl)-S-methylisothiosemicarbazide hydroiodide is made from methyl iodide treatment in refluxing ethanol of 1-(p-chlorobenzyl)thiosemicarbazide, which in turn is made from 4% sodium amalgan in refluxing 80% ethanol reduction of p-chlorobenzaldehyde thiosemicarbazone: E. Hoggarth and E. H. P. Young, J. Chem. Soc., 1582 (1950).

A solution of 0.7 g. (4.5 mmole) of p-chlorobenzylhydrazine and 1.6 g. (4.5 mmole) of 1-(p-chlorobenzyl)-S-methylisothiosemicarbazide hydroiodide in 25 ml. of tetrahydrofuran is heated at reflux for 1 hour, then rotary evaporated to give a semisolid product which is dissolved in 10 ml. of hot tetrahydrofuran and diluted with ether to give an oil which crystallizes on standing in the cold. Collection and recrystallization from chloroform-methylene chloride-ether gives 1,3-bis(4-chlorobenzylamino)guanidine hydroiodide, melting point 142°–145°C.

EXAMPLE 24

Preparation of 1,3-bis(4-Trifluoromethoxybenzylideneamino)guanidine Hydrochloride A micro 3-neck flask filled with 0.60 g. (0.025 g. equivalent) of magnesium turnings is flame-dried under nitrogen, then 5 ml. of anhydrous ether is added followed by 1 ml. of a solution of 5.0 g. (0.021 mole) of p-bromophenyltrifluoromethyl ether in 10 ml. of anhydrous ether. The reaction mixture is stirred under nitrogen for 2 hours or until the Grignard reaction beings; remaining solution is added dropwise, allowing the mixture to reflux from the heat of reaction. After addition is complete, 5 ml. of etheris added and stirring continued an additional ½ hour.

To the resulting Grignard solution is added dropwise with stirring under nitrogen 3.0 g. (0.022 mole) of N-methylformanilide in 5 ml. of ether at such a rate as to cause mild reflux of the mixture. After addition is complete, the reaction mixture is stirred an additional hour and 25 ml. of 10% surfuric acid solution cautiously added dropwise. When all the Mg has dissolved, the aqueous layer is separated and washed with two 20 ml. portions of ether, and the combined ethereal layers washed with saturated sodium bicarbonate solution, water, and saturated sodium chloride solution (20 ml. of each), and dried (magnesium sulfate). Evaporating solvent gives 5.4 g. of a red oil containing about 20% of the desired aldehyde (estimated from integration of the NMR signals for aldehydic and aromatic protons).

The crude aldehyde oil from above is added to a boiling solution of 0.4 g. (3.2 mmole) of diaminoguanidine hydrochloride in 25 ml. of 95% ethanol, cooled, filtered off amorphous material, diluted with 10-fold excess of ether to cloudiness, cooled and filtered to give 1,3-bis(4-trifluoromethoxybenzylideneamino)guanidine hydrochloride, melting point 265°–268°C. (dec.).

Additional material can be obtained from the mother liquors.

I claim:

1. A substituted guanidine of the formula:

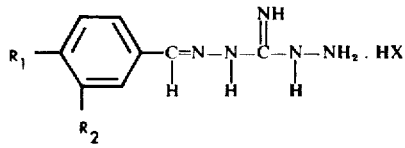

wherein $R_1$ is selected from the group consisting of halogen, trifluoromethyl, trifluoromethoxy and cyano, $R_2$ is hydrogen or chlorine and X is the anion of pharmacologically acceptable acid.

2. The substituted guanidine according to claim 1: 1-amino-3-(4-chlorobenzylideneamino)guanidine hydrochloride.

3. The substituted guanidine according to claim 1: 1-amino-3guanidine hydrochloride.

4. The substituted guanidine according to claim 1: 1-amino-3-(3,4-dichlorobenzylideneamino)guanidine hydrobromide.

5. The substituted guanidine according to claim 1: 1-amino-3-(4-cyanobenzylideneamino)guanidine hydroiodide.

6. The substituted guanidine according to claim 1: 1-amino-3-(4-bromobenzylideneamino)guanidine hydrochloride.

* * * * *

UNITED STATES PATENT OFFICE
CERTIFICATE OF CORRECTION

PATENT NO. : 3,941,825
DATED : March 2, 1976
INVENTOR(S) : ANDREW STEPHEN TOMCUFCIK It is certified that error appears in the above-identified patent and that said Letters Patent are hereby corrected as shown below:

Column 20, line 41, "1-amino-3guanidine hydrochloride." should be -- 1-amino-3-[(4-trifluoromethyl)benzylideneamino]-guanidine hydrochloride. --.

Signed and Sealed this

Twenty-first Day of September 1976

[SEAL]

Attest:

RUTH C. MASON
*Attesting Officer*

C. MARSHALL DANN
*Commissioner of Patents and Trademarks*